United States Patent [19]
Beltz

[11] Patent Number: 5,284,470
[45] Date of Patent: Feb. 8, 1994

[54] WEARABLE, PORTABLE, LIGHT-WEIGHT ARTIFICIAL KIDNEY

[76] Inventor: Alex D. Beltz, 956 Notre Dame St., Upland, Calif. 91786

[21] Appl. No.: 970,041

[22] Filed: Nov. 2, 1992

[51] Int. Cl.⁵ .................. A61F 2/14; A61F 2/12; B01D 11/00; B01D 61/00
[52] U.S. Cl. .................. 604/4; 604/5; 604/6; 604/7; 604/8; 623/66; 210/321.71; 210/646; 210/929
[58] Field of Search .................. 604/4, 5, 6, 7, 8; 210/321.71, 433.1, 645, 646, 929; 623/11, 66, 12; 422/44, 48; 436/177, 178

[56] References Cited

U.S. PATENT DOCUMENTS

| | | | |
|---|---|---|---|
| 4,079,007 | 3/1978 | Hutchisson | 210/321.71 |
| 4,083,777 | 4/1978 | Hutchisson | 210/321.71 X |
| 4,183,811 | 1/1980 | Walch et al. | 210/646 |
| 4,212,738 | 7/1980 | Henne | 210/321.75 X |
| 4,235,231 | 11/1980 | Schindler et al. | 604/4 X |
| 4,850,964 | 7/1989 | Cotter | 604/4 |
| 4,950,395 | 8/1990 | Richalley | 210/321.71 |
| 5,092,886 | 3/1992 | Dobos-Hardy | 623/12 |
| 5,112,298 | 5/1992 | Prince et al. | 604/4 X |

OTHER PUBLICATIONS

"Development of a Portable Dialysing System", Harston et al.

Primary Examiner—Randall L. Green
Assistant Examiner—Dinh X. Nguyen
Attorney, Agent, or Firm—Charles C. Logan, II

[57] ABSTRACT

A portable artificial kidney in the form of a self-contained unit whose size and shape is such that it is lightweight and relatively small. It can be worn or attached to a patient in such a manner that it will not interfere with normal physical activities. The artificial kidney has a blood plasma separator unit that receives impure whole blood from the body of a patient and it separates a predetermined amount of plasma therefrom and returns the remainder of the blood back to the patients body. The separated plasma is then transmitted through a chemical treatment unit where the contaminated plasma is relieved of uric acid, creatinine, phosphate, and ammonium ions. The detoxified plasma is then transmitted to a water removal unit and then the detoxified plasma is returned to the patients circulatory system.

29 Claims, 1 Drawing Sheet

WEARABLE, PORTABLE, LIGHT-WEIGHT ARTIFICIAL KIDNEY

BACKGROUND OF THE INVENTION

The invention relates to a blood detoxification system and more specifically to a structure in the form of a small, light-weight, wearable, artificial kidney.

There are a large number of people throughout the world who have kidneys that do not function properly. The standard treatment for people when they are under medical care is to use a dialysis machine for detoxification of their blood. Some of the major drawbacks of using dialysis machines is they are very expensive, they are very large and heavy, and a patient usually has to be detoxified several times a week. A standard treatment may take four or more hours to complete and it must be done at a medical facility. Also approximately 200 to 300 liters of dialyzing fluid is needed for each dialysis treatment. The dialyzing machines utilize specialized dialyzing membranes that filter out the impurities in the blood as the combined toxic blood and dialyzing fluid are passed therethrough.

More recent advances in the state of the art have been to build a structure in the form of an artificial kidney and these are basically modified versions of the dialyzing machines. Most of the research and development has been directed to the development of better dialyzing membranes, their packaging and sterilization. Some English commercial models automatically sterilize themselves after each dialyzing period. Other research and development work is concerned with a reduction of the 200-300 liters of dialyzing fluid needed for each dialysis. Although there has been much done in the development of blood compatible polymers for the membranes, as yet, none has been found that will transport impure whole blood through the membrane without some undesirable effects.

The goal in detoxifying impure whole blood is the removal of urea, uric acid, creatinine, middle molecular substances (MMS) which have a molecular weight of 1400-1550, water and phosphate from the blood. Urea is the final product of the decomposition and utilization of proteins in the body and it is eliminated through the urine. Uric acid is a substance that is the product of metabolism found normally in urine. Creatinine is a breakdown or waste product of creatine and it is a complex chemical substance, an amino acid, found in animal tissues, especially in muscles. Phosphate is a salt of phosphoric acid and this compound is formed by the replacement of one or more of the hydrogen atoms in phosphoric acid with an atom or atoms of a metal.

Blood clotting is also a major problem for several reasons; (1) ultra filtration for water removal requires a higher hydrostatic pressure than the blood normally encounters. This causes platelet damage with subsequent blood clotting. (2) calcium adheres to dialyzing membranes so that it has to be added to prevent heart damage. (3) Protein tends to adsorb to some polymer walls as well as dialyzing membranes, and this reduces membrane efficiency and aids clotting. (4) Other ions also adsorb on the membranes. Wearable units at this tine utilize dialysate and various means for scrubbing it so as to reduce the amount of dialyzing fluid. Unfortunately, the pumps, plumbing, and dialysate considerably increase the weight of the entire apparatus. At this time the smallest known artificial kidney weighs approximately 70 pounds and it was developed by Dr. Chang. With the use of dialysate almost everything is removed from the blood, thus there is a tendency toward the disequilibrium syndrome which can cause sudden death, anemia, hypertension, hyperkalemia, bone demineralization and calcification, neuro psychiatric problems with transitory psychosis, etc. This means close expensive technical aid for the patient who, of necessity must undergo dialysis. Dr. Chang admits two major problems with his artificial kidney, (1) blood clotting, and (2) water removal.

Because of the weight-volume limits, dialyzing fluid devices cannot be used for a wearable, portable, artificial kidney.

It is an object of the invention to provide a novel artificial kidney that is portable and sufficiently light in weight so it can be worn or carried about by a user.

It is also an object of the invention to provide a novel artificial kidney that is more economical in price thereby reducing the medical cost for a person requiring constant detoxification of their blood.

It is another object of the invention to provide a novel artificial kidney that can be worn by a patient during the day and which will not interfere with normal physical activities.

It is another object of the invention to provide a novel artificial kidney that eliminates the need for dialyzing fluid which in state of the art devices require 200-300 liters of the dialyzing fluid for each dialysis.

It is an additional object of the invention to provide a novel artificial kidney that will have small throw-away packets that are replaced daily.

SUMMARY OF THE INVENTION

The novel artificial kidney is a self-contained assembly weighing less than 15 pounds, and being approximately 150 cubic inches in size. The artificial kidney would be worn or attached to the user and will not interfere with normal physical activities.

The basic components of the novel artificial kidney are a blood plasma separator unit, a chemical treatment unit, and a water removal unit. The system also includes blood access from the patient via an arterial venous shunt (single or double needle) and this would normally be implanted in one of the patients arteries and corresponding veins for a period of time after which it is removed and inserted at another site. The novel artificial kidney would be detachably connected to the arterial venous shunt for transporting the toxic whole blood to the artificial kidney and also returning the detoxified blood back to the patient.

The power source for operation of the flow of blood through the artificial kidney can be through one of two methods. Normally the hydrostatic blood pressure of the patient is sufficient for operating the flow of blood through the artificial kidney. As an alternative, a light-weight pump and battery to produce a slightly negative pressure on the plasma side of the apparatus can be used.

The blood plasma separator would preferably be in the form of a packet and normally it would be replaced daily by the patient. In a preferred embodiment, the blood plasma separator would take the form of an elongated outer tube through which passes an inner tube. Whole blood would enter one end of the blood plasma separator and be directed into the interior of the inner tube that would be made of a polycarbonate perforated membrane. The hole sizes in the perforated membrane would preferably be between 3 microns to 0.45 microns or less. The diameter of the holes is such that they prevent extrusion of formed blood elements (e.g. platelets, red and white corpuscles) while permitting the passing of plasma. A predetermined amount of the plasma will be removed from the toxic arterial blood while the remaining blood corpusles minus some of the plasma is returned to the vascular system. The outer tube of the plasma separator will have urease placed on its inner wall surface to break down urea into ammonium ions and carbon dioxide. Accordingly, the inner tube as it exits the blood plasma separator will have polycythemic blood (i.e. blood with some plasma removed) that is then transmitted back to the patient's body. The area within the outer tube and outside the inner tube would be filled by plasma that has passed through the holes in the polycarbonate perforated membrane structure.

The urease coated tube coming out of the blood plasma separator and going to the chemical treatment packet is used to break down urea (which is not absorbed by activated charcoal). The breakdown results in ammonia ions and carbon dioxide with the ammonium ions being picked up by zirconium phosphate. The outer tube would be made of medically approved blood tubing having an inner diameter of approximately 7 mm. The inner tube has a maximum inner diameter of 3 mm. The concentric tubes could have a convoluted shape as they pass through the blood plasma separator or the concentric tubes could be formed in any other particular shape that would be workable. The polycythemic blood that exits the inner tube is transmitted back to the patient's body. The plasma that exits the end of the outer tube is next transmitted to the chemical treatment unit.

The chemical treatment unit is a removable packet and it functions to relieve the contaminated plasma of uric acid and creatinine by means of activated charcoal. The phosphate ions are removed by zirconium oxide and the ammonium ions are removed by zirconium phosphate. The three major removal identities are activated charcoal (amonium ions, uric acid, and creatinine, MMS), zirconium phosphate (ammonium ions), and zirconium oxide (ammonium ions). These are put in contact with the plasma coming out of the inner tube of the blood separator. The chemical treatment unit is formed of a single tube with no holes in it. The walls of the tube are coated with adsorbents. In addition to removing the uric acid, creatinine, phosphate, and ammonium ions, middle molecular substances (with mole wt. of between 1400 and 1550) are removed.

The plasma after being processed through the chemical treatment unit packet passes as detoxified plasma into the water removal unit packet. This packet has a perforated tube through which passes the detoxified plasma. This tube is formed of a polycarbonate perforated membrane material having holes whose diameter are between 0.45 and less microns or it might be formed of CELLOPHANE. Surrounding the tube would be a high molecular size desiccant (perhaps SEPHADEX) to attract the later. Other similar large molecule desiccants may also be used. The tube in the water removal packet would preferably have a convoluted configuration although other workable configurations might be used. The water removal packet would normally have a color coded indicator to show when it is loaded and needs to be replaced.

The detoxification period and packet replacement will vary from patient to patient. However, maximum daily use should not exceed 12 hours. Daily replacement of the blood plasma separator packet and chemical treatment packet should be acceptable for most patients. The water removal packet would be changed when the color coated indicator shows they are loaded.

The advantages of the artificial kidney are as follows: (1) service of the unit would be by the patient as he could change the replaceable packets. Color indicators in the packets themselves would show when they are to be replaced with fresh ones. The only requirement for the patient would be they check with a physician each week to determine the blood levels of the materials removed by the device. (2) the patient may have small amounts of Heparin (or none at all) added. (3) blood cell damage will be greatly reduced over that with dialysis. (4) shock to the body from quick removal of heightened levels of urea, creatinine, uric acid, and the middle molecular substances will be eliminated (homeostasis promoted). (5) patients cost should be reduced approximately ¼ to 1/6 of the cost now required for a person with non-functioning kidneys.

DESCRIPTION OF THE PREFERRED EMBODIMENT

Figure 1:
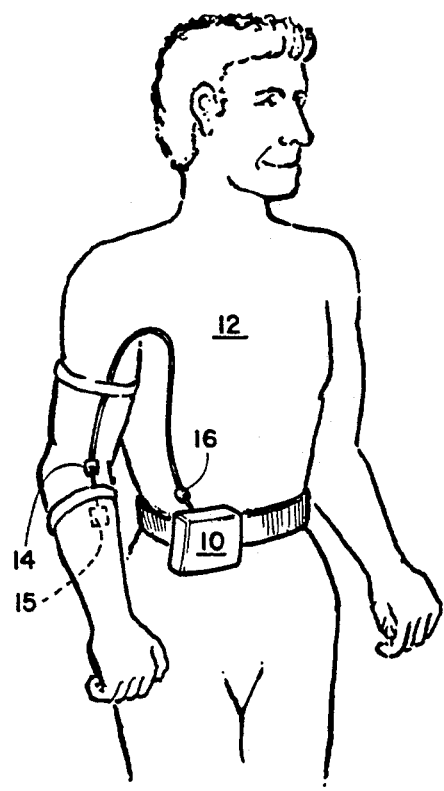
FIG. 1 is a perspective view of a patient wearing the artificial kidney.
Figure 3:
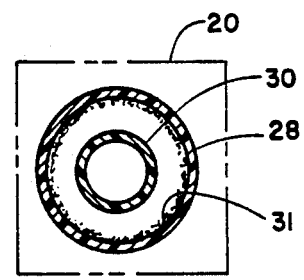
FIG. 3 is a cross sectional view taken through the concentric tubes of the blood separator unit.
Figure 4:
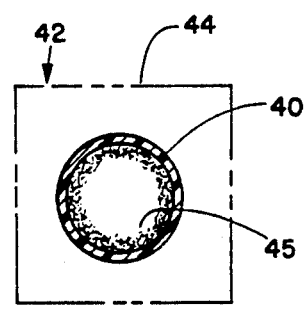
FIG. 4 is a cross sectional view taken through the tube in the chemical treatment unit.
Figure 2:
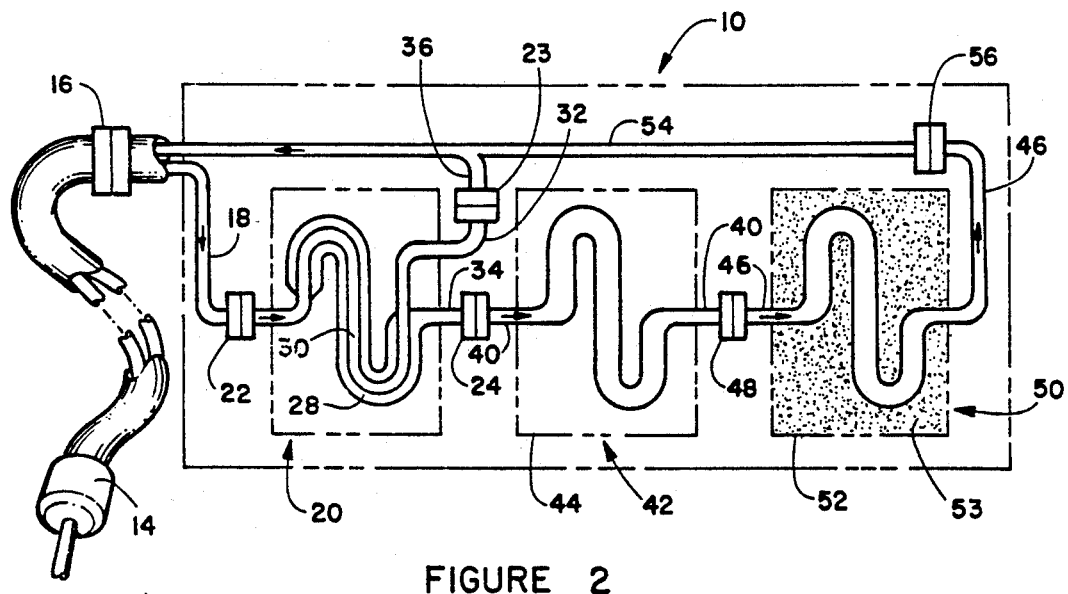
FIG. 2 is a schematic diagram illustrating the components of the artificial kidney and the manner in which it is connected to the body of a patient.

The novel artificial kidney will now be described by referring to FIGS. 1-4 of the drawing. The artificial kidney is generally designated numeral 10.

A patient 12 would have a needle 14 detachably inserted into an arterial venous shunt 15 that has been implanted in his body and connected to an artery and a vein. The position of the shunt would be changed periodically in order to reduce damage to the artery. A quick disconnect assembly 16 connects the tube from needle 14 to a tube 18 that carries toxic blood from the patient to the blood plasma separation unit 20. Quick disconnect assemblies 22, 23 and 24 allow the blood plasma separation unit packet to be easily and quickly removed and replaced. The separation unit has concentric tubes 28 and 30 (See FIG. 3) traveling through a convoluted pattern throughout the length of the separator unit. Tube 28 is standard medically approved blood tubing and it has a coating of urease 31 on its inner surface. Tube 30 would be polycarbonate perforated membrane material with holes in the order of 3 microns to 0.45 microns or less that allow the plasma to separate from the whole blood as it passes through tube 30 under pressure. The separated plasma exits the separator unit through tube 34. Tube 32 is connected to tube 30 and the blood with some of the plasma removed passes through this tube on its return route through tube 36 to the patient.

Tube 40 passes through chemical treatment unit 42 within packet housing 44. The interior surface of tube 40 has adsorbents 45 coated on its inner wall. These adsorbents take uric acid, creatinine, middle molecular substances (with mole weight of between 1400 and 1550), phosphate, and ammonium ions (from the breakdown of urea) from the plasma. Tube 40 is connected to tube 46 by quick-disconnect assembly 48. Tube 46 would preferably have a convoluted design that passes through the water removal unit 50 that has a packet housing 52. A high molecular weight desiccant 53 surrounds tube 46. Tube 46 is formed of polycarbonate perforated membrane material with holes in it in the order of 0.45 microns or less that allow the water in the plasma to be forced out through its outer walls into the desiccant.

Detoxified plasma exits water removal unit 50 through tube 46 and it is connected to tube 54 by a quick disconnect assembly 56. The other end of tube 54 is connected to quick disconnect assembly 16.

The artificial kidney could be produced in the form of a belt, vest or any other type of wearable structure. Upon removal of the device from the body at night, the contents of the device are expressed back into the body.

What is claimed is:

1. A wearable, portable, light-weight artificial kidney comprising:
   a first means for transmitting impure whole blood from a body of a patient to an artificial kidney;
   a separator means configured to separate a predetermined amount of plasma from said whole blood and a second whole means for returning a remainder of said blood with some of the plasma removed back to the patient's body;
   a means configured to chemically treat and cleanse the plasma that has been separated from the whole blood;
   a means configured to remove water from the plasma that has been separated from the whole blood;
   a third means configured to return the cleansed plasma to the patient's body; and
   wherein said artificial kidney is shaped and sized to be completely worn daily on the body of the patient and weighs less than 15 pounds.

2. A wearable, portable, light-weight artificial kidney as recited in claim 1 further comprising an arterial venous shunt that is detachably interconnected to said first means, said second means and said third means.

3. A wearable, portable, light-weight artificial kidney as recited in claim 2 wherein said arterial venous shunt is configured to be surgically implanted in the body of the patient.

4. A wearable, portable, light-weight artificial kidney as recited in claim 1 wherein said artificial kidney is in the form of a unit that is part of a belt that is sized and shaped to be worn by a patient.

5. A wearable, portable, light-weight artificial kidney as recited in claim 1 wherein said separator means comprises a packet housing having a predetermined length of polycarbonate tubing having holes in side walls of said tubing in a range of 0.4—3.0 microns through which plasma passes, said polycarbonate tubing passing concentrically through an interior of a conventional medically approved blood tubing.

6. A wearable, portable, light-weight artificial kidney as recited in claim 5 wherein said concentrically positioned polycarbonate tubing is formed in a convoluted shape that extends from an inlet end of said separator pack housing to an outlet end.

7. A wearable, portable, light-weight artificial kidney as recited in claim 5 wherein said medically approved blood tubing has an inner surface treated with urease.

8. A wearable, portable, light-weight artificial kidney as recited in claim 1 wherein said means for chemically treating and cleansing the plasma that has been separated from the whole blood comprises a packet housing having a predetermined length of tubing through which said plasma passes, said tubing having an inner surface coated with predetermined adsorbents for removing toxics from said plasma.

9. A wearable, portable, light-weight artificial kidney as recited in claim 1 wherein said means for removing water from the plasma that has been separated from the whole blood comprises a packet housing having a predetermined length of polycarbonate tubing having holes in its side walls in the range of 0.45 microns or less through which water passes, the interior of said packet having predetermined desiccants that absorb water.

10. A wearable, portable, light-weight artificial kidney comprising:
    a first means for transmitting impure whole blood from a body of a patient to an artificial kidney;
    a separator means configured to continuously and non-cyclically separate a predetermined amount of plasma from said whole blood and a second whole means for continuously and non-cyclically returning a remainder of said blood with some of the plasma removed back to the patient's body;
    a means configured to continuously and non-cyclically chemically treat and cleanse the plasma that has been separated from the whole blood;
    a third means configured to continuously and non-cyclically return the cleansed plasma to the patient's body, wherein said artificial kidney is shaped and sized to be completely worn daily on the body of the patient.

11. A wearable, portable, light-weight artificial kidney as recited in claim 10 further comprising an arterial venous shunt that is detachably interconnected to said first means, said second means and said third means.

12. A wearable, portable, light-weight artificial kidney as recited in claim 11 wherein said arterial venous shunt is configured to be surgically implanted in the body of the patient.

13. A wearable, portable, light-weight artificial kidney as recited in claim 10 wherein said artificial kidney is in the form of a unit that is part of a belt that is sized and shaped to be worn by a patient.

14. A wearable, portable, light-weight artificial kidney as recited in claim 10 wherein said artificial kidney is shaped and sized to be completely worn on the body of the patient and weighs less than 15 pounds.

15. A wearable, portable, light-weight artificial kidney as recited in claim 10 wherein said separator means comprises a packet housing having a predetermined length of polycarbonate tubing having holes in side walls of said tubing in a range of 0.4–3.0 microns through which plasma passes, said polycarbonate tubing passing concentrically through an interior of a conventional medically approved blood tubing.

16. A wearable, portable, light-weight artificial kidney as recited in claim 15 wherein said concentrically positioned polycarbonate tubing is formed in a convoluted shape that extends from an inlet end of said separator pack housing to an outlet end.

17. A wearable, portable, light-weight artificial kidney as recited in claim 15 wherein said medically approved blood tubing has an inner surface treated with urease.

18. A wearable, portable, light-weight artificial kidney as recited in claim 10 wherein said means for chemically treating and cleansing the plasma that has been separated from the whole blood comprises a packet housing having a predetermined length of tubing through which said plasma passes, said tubing having an inner surface coated with predetermined adsorbents for removing toxics from said plasma.

19. A wearable, portable, light-weight artificial kidney as recited in claim 10 wherein said means for removing water from the plasma that has been separated from the whole blood comprises a packet housing having a predetermined length of polycarbonate tubing having holes in its side walls in the range of 0.45 microns or less through which water passes, the interior of said packet having predetermined desiccants that absorb water.

20. A wearable, portable, light-weight artificial kidney comprising:
- a first means for transmitting impure whole blood from a body of a patient to an artificial kidney;
- a separator means configured to separate at substantially normal blood pressure a predetermined amount of plasma from said whole blood and a second whole means for returning at substantially normal blood pressure a remainder of said blood with some of the plasma removed back to the patient's body;
- a means configured to chemically treat and cleanse the plasma that has been separated from the whole blood; and
- a third means configured to return at substantially normal blood pressure the cleansed plasma to the patient's body, wherein said artificial kidney is shaped and sized to be completely worn daily on the body of the patient.

21. A wearable, portable, light-weight artificial kidney as recited in claim 20 further comprising an arterial venous shunt that is detachably interconnected to said first means, said second means and said third means.

22. A wearable, portable, light-weight artificial kidney as recited in claim 21 wherein said arterial venous shunt is configured to be surgically implanted in the body of the patient.

23. A wearable, portable, light-weight artificial kidney a recited in claim 20 wherein said artificial kidney is in the form of a unit that is part of a belt that is sized and shaped to be worn by a patient.

24. A wearable, portable, light-weight artificial kidney as recited in claim 20 wherein said artificial kidney is shaped and sized to be completely worn daily on the body of the patient and weighs less than 15 pounds.

25. A wearable, portable, light-weight artificial kidney as recited in claim 20 wherein said separator means comprises a packet housing having a predetermined length of polycarbonate tubing having holes in side walls of said tubing in a range of 0.4–3.0 microns through which plasma passes, said polycarbonate tubing passing concentrically through an interior of a conventional medically approved blood tubing.

26. A wearable, portable, light-weight artificial kidney as recited in claim 25 wherein said concentrically positioned polycarbonate tubing is formed in a convoluted shape that extends from an inlet end of said separator pack housing to an outlet end.

27. A wearable, portable, light-weight artificial kidney as recited in claim 25 wherein said medically approved blood tubing has an inner surface treated with urease.

28. A wearable, portable, light-weight artificial kidney as recited in claim 20 wherein said means for chemically treating and cleansing the plasma that has been separated from the whole blood comprises a packet housing having a predetermined length of tubing through which said plasma passes, said tubing having an inner surface coated with predetermined adsorbents for removing toxics from said plasma.

29. A wearable, portable, light-weight artificial kidney as recited in claim 20 wherein said means for removing water from the plasma that has been separated from the whole blood comprises a packet housing having a predetermined length of polycarbonate tubing having holes in its side walls in the range of 0.45 microns or less through which water passes, the interior of said packet having predetermined desiccants that absorb water.

* * * * *